United States Patent [19]
Archibald et al.

[11] 3,971,787
[45] *July 27, 1976

[54] (4-QUINOLYLAMINO)BENZAMIDES

[75] Inventors: John Leheup Archibald, Windsor; John Arnott Boyle; John Christopher Saunders, both of Maidenhead, all of England

[73] Assignee: John Wyeth & Brother Limited, Taplow, England

[ * ] Notice: The portion of the term of this patent subsequent to Apr. 1, 1992, has been disclaimed.

[22] Filed: Jan. 23, 1975

[21] Appl. No.: 543,217

Related U.S. Application Data

[63] Continuation-in-part of Ser. No. 334,799, Feb. 22, 1973, Pat. No. 3,875,165.

[30] Foreign Application Priority Data

Feb. 5, 1973 United Kingdom.................. 5531/73

[52] U.S. Cl. ..................... 260/286 R; 260/287 AR; 424/258
[51] Int. Cl.$^2$................ C07D 215/44; C07D 401/12
[58] Field of Search ............................ 260/287 AR

[56] References Cited
UNITED STATES PATENTS 3,875,165    2/1973    Archibald et al. .................. 260/287

Primary Examiner—Nicholas S. Rizzo
Assistant Examiner—David E. Wheeler

[57] ABSTRACT 3-(7-Halo-4-quinolyl)-N-[di(loweralkyl)amino(lower alkyl)]-N-(lower alkyl)benzamides and 4-(7-halo-4-quinolyl)-N-[di(lower alkyl)amino(loweralkyl)]-N-(lower alkyl)benzamides and their pharmaceutically acceptable acid addition salts exhibit interesting anti-inflammatory activity. They also exhibit anti-malarial activity and anti-hypertensive activity.

2 Claims, No Drawings

(4-QUINOLYLAMINO)BENZAMIDES

This application is a continuation-in-part of United States Pat. Ser. No. 334,799 entitled "4-Aminoquinoline Derivatives" filed Feb. 22, 1973 in the names of John Leheup Archibald, John Terence Arnott Boyle and John Christopher Saunders, now U.S. Pat. No. 3,875,165, granted Apr. 1, 1975 and entitled "(4-Quinolylamino)-(N-Piperidyl) Benzamides and N-[(4-Quinolylamino)Benzoyl]Piperidines."

The invention provides new 4-aminoquinoline derivatives of the general formula

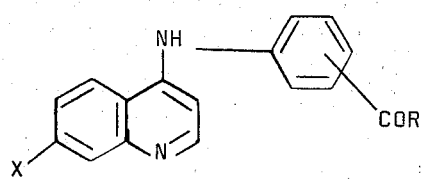

(I)

and their pharmaceutically acceptable acid addition salts, where X is a halogen atom, R represents a group of the formula

—NR$_3$—A—NR$_1$R$_2$ wherein —A—NR$_1$R$_2$ represents a di(loweralkyl)amino(lower alkyl) group and R$_3$ represents a lower alkyl group, and the group —COR is in the meta or para position relative to the 7-halo-4-quinolylamino group.

In the compounds of the invention, X represents a halogen atom, preferably chlorine or bromine. In formula I the group denoted by —COR is in the m- or p-position, advantageously the p- position, with respect to the 7-halo-4-quinolylamino group. R$_1$, R$_2$, R$_3$ and A are independently lower alkyl. As examples of lower alkyl there may be mentioned, for example, methyl, ethyl, n- or i- propyl and n-butyl.

The term "lower" as used herein in connection with such groups as "alkyl" denotes that the group contains up to 6 carbon atoms, preferably up to 4 carbon atoms.

Examples of acid addition salts are those formed from inorganic and organic acids and in particular pharmaceutically acceptable acid addition salts such as the sulphate, hydrochloride, hydrobromide, hydroiodide, nitrate, phosphate, sulphonate (such as the methanesulphonate and p-toluenesulphonate), acetate, maleate, fumarate, tartrate, malonate, citrate and formate.

The new compounds of the invention where the group —COR is in the meta position have the formula

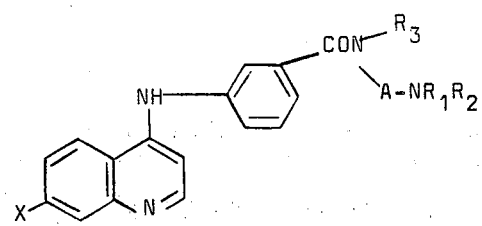

(II)

wherein X, A, R$_1$, R$_2$ and R$_3$ are as defined above. They may be termed "3-(7-halo-4-quinolylamino)-N-[di(-loweralkyl)amino(loweralkyl)]-N-(loweralkyl)benzamides."

The new compounds of the invention where the group —COR is in the para position have the formula

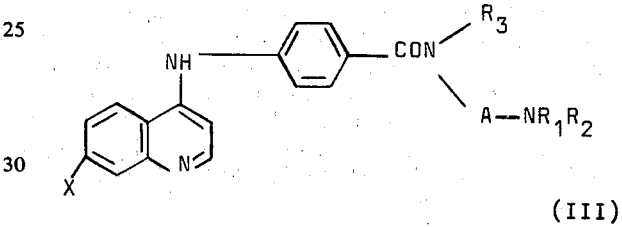

(III)

where X, A, R$_1$, R$_2$ and R$_3$ are as defined above. They may be termed "4-(7-halo-4-quinolylamino)-N-[di(-loweralkyl)amino(loweralkyl]-N-(loweralkyl)benzamides."

The compounds of the invention may be made by building the compound up by known reactions. In particular the amide linkage shown in formula I as —COR may be formed by acylation of an appropriate amine, and an amino- substituted benzamide may be converted to the secondary amine by introducing the 7-halo-4-quinolyl group in known manner.

The invention provides a method of making compounds of the formula I and their acid addition salts wherein a. a compound of the formula HNR$_2$—A—NR$_1$R$_2$, wherein R$_1$, R$_2$, R$_3$ and A are as defined in connection with formula I, is acylated with a compound of formula (IV) or (V)

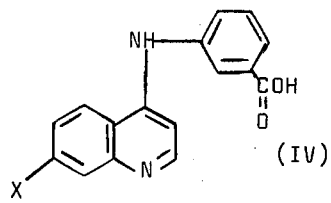

(IV)

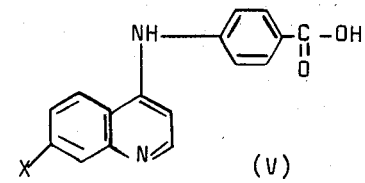

(V)

(wherein X is halogen connection with formula I), or a reactive derivative of the compound of formula (IV) or (V); or b. a compound of the formula (VI) or (VII)

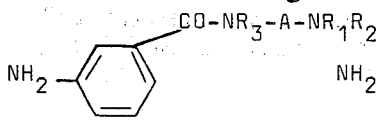 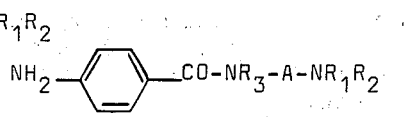

(VI)            (VII)

(where $R_1$, $R_2$, $R_3$ and A are as defined in connection with formula I) is reacted with a compound of formula (VIII)

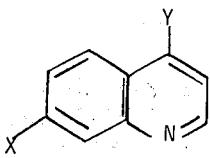

(VIII)

(where X is halogen and Y denotes a group or atom replaceable by nucleophilic attack by compound of formula VI or VII). Y is for example, an iodine atom, a bromine atom or a chlorine atom or an organosulphonyloxy group, for instance, p-toluenesulphonyloxy. If desired the process may also include conversion of a free base form of compound of formula I into an acid addition salt form or conversion of an acid addition salt form of a compound of formula I into the corresponding free base form.

Starting materials of formula $HNR_3$—A—$NR_1R_2$ and formulae IV, V, VI, VII and VIII are known compounds or, if new, are accessible by conventional methods.

The acylation method may be carried out by reacting the compound of formula IV or V with the compound of formula RH in the presence of a condensing agent, for instance, a carbodiimide. The reactive acylating derivatives of the compound of formula IV or V may be employed, for example, active esters, acyl halides, simple or mixed anhydrides and the acid azide. The acid halides, particularly the acid chloride are especially suitable. The acylation product may be recovered from the reaction mixture by standard isolation procedures.

Compounds of the formulae VI and VII are accessible in standard manner, for example, by acylation of a compound of formula RH where R has the meanings given in connection with formula I with an acylating derivative of a m- or p- nitrobenzoic acid or m- or p- (protected amino) benzoic acid and subsequent reduction of the nitro group or removal of the amino protecting group. The reaction of the primary amine VI or VII with the compound of formula VIII may be carried out in conventional manner for amination of 4-substituted quinolines. The reaction products may be recovered from the reaction mixtures by standard isolation procedures.

The compounds of the present invention may be isolated in free base form or as acid addition salts. Acid addition salts may be converted into the free bases in conventional manner. The free base forms may be converted into acid addition salts in conventional manner, for instance, by adding ethereal hydrogen chloride to a solution of the free base where a hydrochloride salt is desired.

The compounds of the present invention are indicated for pharmacological usage. In particular, the compounds of the invention demonstrate interesting anti-inflammatory activity and also, demonstrate anti-malarial activity and anti-hypertensive activity. A literature reference for a procedure for testing for anti-inflammatory activity is Newbould, B.B. Brit. Jour.-Pharm.Chemoth., 21, 127–136 (1963).

The invention also includes pharmaceutical compositions containing as active ingredients a compound of formula (I) or a pharmaceutically acceptable acid addition salt thereof, which may be micronised if desired. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely divided active ingredient in aqueous starch or sodium carboxymethyl cellulose solution, or in a suitable oil, for instance arachis oil. Liquid pharmaceutical compositions which are sterile or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit dosages containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form. The invention is illustrated by the following examples:

EXAMPLE 1

4-(7-Chloro-4-quinolylamino)-N-(2-diethylaminoethyl)-N-ethyl-benzamide 4-(7-Chloro-4-quinolylamino) benzoyl chloride hydrochloride (prepared by refluxing 9.0 grams of 4-(7-chloro-4-quinolylamino) benzoic acid and evaporating the excess thionyl chloride, was added in portions to a cooled, stirred mixture of 4.32 grams of N,N,N¹-triethylethylene diamine and 32 grams of sodium carbonate in 60 milliliters of chloroform and 70 milliliters of water. After stirring for 2 days at room temperature the reaction mixture was filtered, the chloroform layer separated, dried and evaporated to give an oil. This was triturated with hexane to give a light brown solid, which was triturated with acetone to give 5.3 grams of the title compound as a quarter hydrate.
Melting point 166°C. Analysis: found C, 67.2%; H, 7.06%; N, 12.9%; $C_{24}H_{29}ClN_4O$. 1/4 $H_2O$ requires C, 67.1%; H, 6.93%; N, 13.0%.

EXAMPLE 2

3-(7-Chloro-4-quinolylamino)-N-(2-diethylaminoethyl)-N-ethyl-benzamide 3-(7-Chloro-4-quinolylamino)benzoyl chloride hydrochloride (prepared from the acid by refluxing with thionyl chloride and evaporating excess thionyl chloride) is reacted with N,N,N¹-triethylethylene diamine in a similar manner to Example 1 to give the title compound.

EXAMPLE 3

4-(7-Chloro-4-quinolylamino)-N-(4-dimethylaminobutyl)-N-propyl-benzamide 4-(7-Chloro-4-quinolylamino)benzoyl chloride hydrochloride is reacted with 1-dimethylamino-4-propylaminobutane in a similar manner to Example 1 to give the title compound.

We claim:

1. A compound selected from those having the formulae

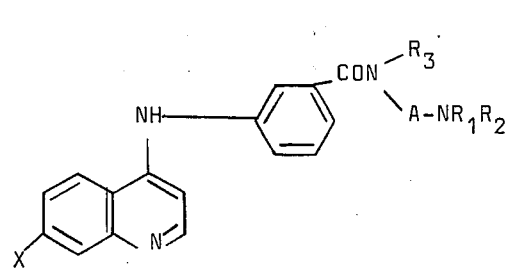

(II)

and

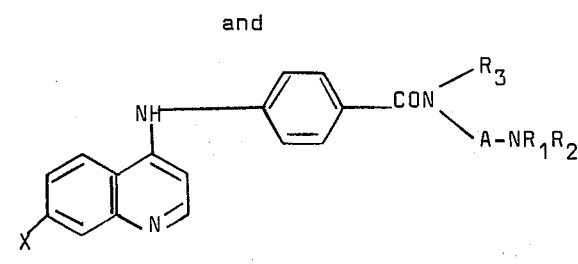

(III)

and their pharmaceutically acceptable acid addition salts, wherein X is halogen, the group $-A-NR_1R_2$ is di(lower alkyl) amino(lower alkyl) and $R_3$ is lower alkyl.

2. A compound as defined in claim 1, which is selected from 4-(7-Chloro-4-quinolylamino)-N-(2-diethylaminoethyl)-N-ethyl-benzamide and its pharmaceutically acceptable acid addition salts.

* * * * *